(12) United States Patent
Nathaniel et al.

(10) Patent No.: US 9,109,998 B2
(45) Date of Patent: Aug. 18, 2015

(54) METHOD AND SYSTEM FOR STITCHING MULTIPLE IMAGES INTO A PANORAMIC IMAGE

(75) Inventors: Ram Nathaniel, Tel Aviv (IL); Dan Rappaport, Tel Aviv (IL); Ishay Goldin, Tel Aviv (IL)

(73) Assignee: ORTHOPEDIC NAVIGATION LTD., Ramat Hasharon (IL)

( * ) Notice: Subject to any disclaimer, the term of this patent is extended or adjusted under 35 U.S.C. 154(b) by 901 days.

(21) Appl. No.: 12/999,364

(22) PCT Filed: Jun. 18, 2009

(86) PCT No.: PCT/IL2009/000605
§ 371 (c)(1),
(2), (4) Date: Apr. 13, 2011

(87) PCT Pub. No.: WO2009/153789
PCT Pub. Date: Dec. 23, 2009

(65) Prior Publication Data
US 2011/0188726 A1    Aug. 4, 2011

Related U.S. Application Data

(60) Provisional application No. 61/073,385, filed on Jun. 18, 2008.

(51) Int. Cl.
*G06K 9/00* (2006.01)
*G01N 23/04* (2006.01)
*G06T 3/40* (2006.01)

(52) U.S. Cl.
CPC .............. *G01N 23/04* (2013.01); *G06T 3/4038* (2013.01); *G06T 2207/10121* (2013.01); *G06T 2207/30008* (2013.01)

(58) Field of Classification Search
None
See application file for complete search history.

(56) References Cited

U.S. PATENT DOCUMENTS

| 581,540 | A | 4/1897 | Dennis |
| 1,396,920 | A | 11/1921 | Brostrom |
| 2,819,526 | A | 1/1958 | Brown, Jr. |
| 3,706,883 | A | 12/1972 | McIntyre |

(Continued)

FOREIGN PATENT DOCUMENTS

| EP | 0655861 A1 | 5/1995 |
| EP | 1255403 A3 | 3/2004 |
| EP | 1498849 A2 | 1/2005 |
| EP | 1632181 B1 | 11/2007 |
| WO | WO2006114721 A2 | 11/2006 |
| WO | WO2009022266 A1 | 2/2009 |
| WO | WO2011042832 A1 | 4/2011 |

OTHER PUBLICATIONS

B.K.P. Horn and M.J. Brooks, "Shape from Shading" MID Press, Cambridge Mass (1989).

(Continued)

*Primary Examiner* — Avinash Yentrapati
(74) *Attorney, Agent, or Firm* — Vladimir Sherman; Professional Patent Solutions

(57) ABSTRACT

Disclosed is a method for generating a panoramic image of a region of interest (ROI) which is larger than a field of a view of a radiation based imaging device, comprising, positioning markers along the ROI, acquiring a set of images along the ROI, wherein the acquired images have at least partially overlapping portions, aligning at least two separate images by aligning a common marker found in both images and compensating for a difference between a distance from a radiation source to the marker element and the distance from the radiation source to a plane of interest.

14 Claims, 7 Drawing Sheets

(56) References Cited

U.S. PATENT DOCUMENTS

| | | | |
|---|---|---|---|
| 3,770,956 A | 11/1973 | Johnson | |
| 3,848,136 A | 11/1974 | Seldin | |
| 4,005,527 A | 2/1977 | Wilson et al. | |
| 4,736,399 A | 4/1988 | Okazaki | |
| 4,890,311 A | 12/1989 | Saffer | |
| 4,915,112 A | 4/1990 | Singer | |
| 4,918,715 A | 4/1990 | Krupnick et al. | |
| 5,052,035 A | 9/1991 | Krupnick | |
| 5,123,056 A | 6/1992 | Wilson | |
| 5,262,856 A | 11/1993 | Lippman et al. | |
| 5,285,785 A | 2/1994 | Meyer | |
| 5,400,513 A | 3/1995 | Duffield | |
| 5,409,004 A | 4/1995 | Sloan | |
| 5,551,160 A | 9/1996 | Ferris et al. | |
| 5,640,436 A | 6/1997 | Kawai et al. | |
| 5,649,032 A | 7/1997 | Burt et al. | |
| 5,687,331 A | 11/1997 | Volk et al. | |
| 5,801,385 A | 9/1998 | Endo et al. | |
| 5,833,607 A | 11/1998 | Chou et al. | |
| 5,841,833 A | 11/1998 | Mazess et al. | |
| 5,970,119 A | 10/1999 | Hofmann | |
| 6,075,879 A | 6/2000 | Roehrig et al. | |
| 6,097,833 A * | 8/2000 | Lobregt et al. | 382/130 |
| 6,101,238 A * | 8/2000 | Murthy et al. | 378/62 |
| 6,196,715 B1 * | 3/2001 | Nambu et al. | 378/197 |
| 6,206,566 B1 | 3/2001 | Schuetz | |
| 6,243,439 B1 | 6/2001 | Arai et al. | |
| 6,356,621 B1 | 3/2002 | Furumori et al. | |
| 6,396,903 B1 | 5/2002 | Wenstrup | |
| 6,618,494 B1 | 9/2003 | Nonay et al. | |
| 6,666,579 B2 | 12/2003 | Jensen | |
| 6,792,071 B2 | 9/2004 | Dewaele | |
| 6,925,200 B2 | 8/2005 | Wood et al. | |
| 6,990,229 B2 | 1/2006 | Ohishi | |
| 7,015,906 B2 | 3/2006 | Olschewski et al. | |
| 7,396,161 B2 | 7/2008 | Schmitt | |
| 7,453,977 B2 | 11/2008 | DiBianca et al. | |
| 7,499,579 B2 | 3/2009 | Squilla et al. | |
| 7,611,466 B2 | 11/2009 | Chalana et al. | |
| 7,664,298 B2 | 2/2010 | Lang et al. | |
| 7,702,380 B1 | 4/2010 | Dean | |
| 7,773,829 B1 | 8/2010 | Brandt | |
| 7,797,030 B2 | 9/2010 | Lahm et al. | |
| 7,871,406 B2 | 1/2011 | Nields et al. | |
| 7,877,128 B2 | 1/2011 | Schwartz | |
| 7,905,924 B2 | 3/2011 | White | |
| 7,995,822 B2 * | 8/2011 | Lang et al. | 382/128 |
| 8,090,166 B2 | 1/2012 | Rappaport et al. | |
| 8,104,958 B2 * | 1/2012 | Weiser et al. | 378/207 |
| RE43,282 E | 3/2012 | Alexander et al. | |
| 8,463,006 B2 | 6/2013 | Prokoski | |
| 8,611,697 B2 | 12/2013 | Nathaniel et al. | |
| 8,855,390 B2 | 10/2014 | Bismuth et al. | |
| 2002/0077540 A1 | 6/2002 | Kienzle, III | |
| 2003/0014034 A1 | 1/2003 | Strobel | |
| 2004/0034298 A1 | 2/2004 | Johnson et al. | |
| 2004/0086082 A1 | 5/2004 | Foos et al. | |
| 2004/0111024 A1 | 6/2004 | Zheng et al. | |
| 2005/0104018 A1 | 5/2005 | Chang et al. | |
| 2005/0213849 A1 * | 9/2005 | Kreang-Arekul et al. | 382/284 |
| 2006/0120583 A1 | 6/2006 | Dewaele | |
| 2006/0154198 A1 | 7/2006 | Durbin et al. | |
| 2006/0177150 A1 * | 8/2006 | Uyttendaele et al. | 382/284 |
| 2007/0041508 A1 | 2/2007 | Tubbs | |
| 2008/0056547 A1 * | 3/2008 | Kokubun et al. | 382/128 |
| 2008/0111831 A1 * | 5/2008 | Son et al. | 345/629 |
| 2008/0118023 A1 | 5/2008 | Besson | |
| 2008/0242971 A1 | 10/2008 | Klingenbeck-Regn | |
| 2009/0059018 A1 * | 3/2009 | Brosnan | 348/218.1 |
| 2009/0221908 A1 | 9/2009 | Glossop | |
| 2009/0310845 A1 * | 12/2009 | Ogawa et al. | 382/132 |
| 2010/0135467 A1 * | 6/2010 | King et al. | 378/163 |
| 2010/0232670 A1 | 9/2010 | Blanchard et al. | |
| 2011/0019884 A1 | 1/2011 | Blau | |
| 2011/0102461 A1 * | 5/2011 | Schultz et al. | 345/643 |
| 2011/0188726 A1 | 8/2011 | Nathaniel et al. | |
| 2012/0059248 A1 | 3/2012 | Holsing et al. | |
| 2013/0211244 A1 | 8/2013 | Nathaniel | |
| 2013/0322726 A1 | 12/2013 | Nathaniel | |

OTHER PUBLICATIONS

Harris, J.H., "The normal cervical spine" (1987). (Web-link: http://rapidshare.com/files/213791249/TheNormalCervicalSpine.pdf. html).

Segonne, Florent, "Segmentation of Medical Images under Topological Constraints", 2005, USA.

Maintz, et al.; "A Survey of Medical Image Registration"; 1998; pp. 1-37; pp. 1-3, 7-142; The Netherlands.

Russakoff, et al., "Fast Intensity-based 2D-3D Image Registration of Clinical Data Using Light Fields", 2003, pp. 1-7, USA.

Chen, et al., "Automatic Extraction of Femur Contours from Hip X-ray Images", 2005, pp. 1-10, Singapore.

Kass, et al., "Snakes: Active Contour Models", 1988, pp. 321-331. The Netherlands.

Long, et al., "Segmentation and feature extraction of cervical spine x-ray images", 1999, pp. 1037-1046, USA.

Zitova, et al., "Image registration methods: a survey", 2003, pp. 977-1000, Czech Republic.

Lee, et al., "Image Morphing Using Deformation Techniques", 1996, pp. 3-23, Korea.

Parkinson, et al., "Methodological principles for factual analysis of trabecular bone", 2000, pp. 134-142, Australia.

Geraets, et al., "The Radiographic Trabecular Pattern of Hips in Patients With Hip Fractures and in Elderly Control Subjects", 1998, pp. 165-173, The Netherlands.

Geraets, et al., "Analysis of the radiographic trabecular pattern", 1991, pp. 575-581, The Netherlands.

Dougherty, et al., "Lacunarity analysis of spatial pattern in CT images of vertebral trabecular bone for assessing osteoporosis", 2002, pp. 129-138, Kuwait.

Behiels, et al, "Evaluation of image features and search strategies for segmentation of bone structures in radiographs using Active Shape Models", 2002, pp. 47-62, Belgium.

Lum, et al., "Cominging Classifiers for Bone Fracture Detection in X-ray Images", 2005, pp. 1149-1152, Singapore.

Cocosco, et al., "BrainWeb: Online Interface to a 3D MRI Simulated Brain Database", 1997, S425-27, Canada.

Maintz, et al.; "An Overview of Medical Image Registration Methods"; 1998; pp. 1-22; The Netherlands.

Joskowicz L et al: "Long Bone Panoramas From Fluoroscopic X-Ray Images", IEEE Transactions on Medical Imaging, IEEE Service Center, Piscataway, NJ, US, vol. 23, No. 1, Jan. 1, 2004, pp. 26-35, XP011104510, ISSN: 0278-0062, DOI: DOI:10.1109/TMI.2003.819931.

Peter Messmer et al: "Image Fusion for Intraoperative Control of Axis in Long Bone Fracture Treatment", European Journal of Trauma, Urban & Vogel, MU, vol. 32, No. 6, Dec. 1, 2006, pp. 555-561, XP019462173, ISSN: 1615-3146, DOI: DOI:10.1007/S00068-006-5159-5.

Foley et al: "Virtual fluoroscopy", Operative Techniques in Orthopaedics, Saunders, Philadelphia, PA, US, vol. 10, No. 1, Jan. 1, 2000, pp. 77-81, XP005183642, ISSN: 1048-6666, DOI:10.1016/S1048-6666(00)80046-4.

Brodke D et al: "Image guidance for spinal surgery", Operative Techniques in Orthopaedics, Saunders, Philadelphia, PA, US, vol. 13, No. 3, Jul. 1, 2003, pp. 152-158, XP004677528, ISSN: 1048-6666, DOI: 10.1016/S1048-6666(03)00020-X.

Amir Herman et al: "Computer-assisted surgery for dynamic hip screw, using Surgix, a novel intraoperative guiding system", The International Journal of Medical Robotics and Computer Assisted Surgery, vol. 5, No. 1, Mar. 1, 2009, pp. 45-50, XP055133701, ISSN: 1478-5951, DOI: 10.1002/rcs.231.

* cited by examiner

METHOD AND SYSTEM FOR STITCHING MULTIPLE IMAGES INTO A PANORAMIC IMAGE

FIELD OF THE INVENTION

The invention is related to the field of medical radiation based imaging. More specifically, the invention relates to the stitching or combining of several images into one panoramic image.

BACKGROUND OF THE INVENTION

Fluoroscopic x-ray images play a key-role in a variety of surgical procedures, e.g., fracture reduction, pedicle screw insertion and implant positioning for treating hip fractures. The surgeon uses the mobile fluoroscopic x-ray machine (C-arm) in the operation room (OR), to determine the position and orientation of bones, implants and surgical instruments. X-ray fluoroscopy instruments have several limitations, one of which is a narrow field of view (FOV) which prevents imaging a large region of interest (ROI), e.g., in the case of long implants placement. A way to address this issue is to acquire several individual overlapping images of the ROI and to compose the equivalent of a single x-ray image by finding adequate correlation between the single images. The final panoramic (or mosaic) image may therefore be several times wider than the original field of view of the apparatus.

Panoramic x-ray views can be useful during various stages of many orthopedic surgery procedures. Preoperatively, they serve for diagnosis and measurements. Intraoperatively, where they are particularly useful, they help avoid positioning errors and enable the surgeon to have a global, unornamented vision of the ROI. Postoperatively, they can also provide useful information concerning the outcome of the surgery.

Panoramic X ray imaging is useful in other areas of medical imaging as well, including cardiovascular angiography of long blood vessels and Digital Radiography (DR) of skeleton parts such as the spine or legs. Modem DR is based on digital X ray detectors which are typically limited in coverage to 43 cm. Longer anatomies are imaged by taking several overlapping images and stitching them together.

Creating panoramic views out of individual images is known in the prior art, and constitutes a very active field of research in the domain of graphic computing. Techniques for composing a panoramic image are disclosed for example in U.S. Pat. No. 5,262,856 and a method for automatic alignment of individual overlapping pictures can be found in U.S. Pat. No. 5,649,032. In brief, generation of panoramic images requires three distinct steps: 1) correcting the distortion of each single image, generally caused by the optical system, 2) alignment and stitching of the individual images and 3) composing the final panoramic image. Several publications relate to methods for correcting optical distortion in x-ray digital imaging such as U.S. Pat. Nos. 4,736,399 or 6,618,494. However, the most difficult step remains aligning and stitching the individual pictures.

To illustrate geometrical difficulties in generating a panoramic image we consider an x-ray imaging system 100 as shown schematically in FIG. 1, x-ray source 102 emits conical beam 104 which is received by area detector 106. System 100 is used to generate one X ray image at a first position and then both the source 102 and detector 106 are translated laterally by a distance X and used to generate a second image at a second position. Objects A,B,C and D represent features of interest in the imaging field. Object A in plane 108 is in the overlap region of the two images so it appears in both images.

In order to stitch the images, object A may be identified in each of the two images and the images translated relative to each other till the object accurately overlaps in the two images. Under these conditions other features in plane 108 will appear focused in the stitched panoramic image. However, object B in plane 110 will appear blurred or doubled in the stitched image, and object C and D in plane 110 (which are not in overlap region) will appear focused but at the wrong distance between them.

In general, image alignment can only be achieved at a certain distance from the x-ray source, a surface known as the plane of interest (POI). Despite its name, The POI is not limited to a single spatial plane, for example, in a whole leg panoramic image, it is sometimes useful to stitch along both the (possibly different) femur and the tibia planes. In fact, the POI can be any continuous spatial surface between the x-ray source and the detector. Stitching of images according to a certain POI causes objects out of the POI to be "blurred", a phenomenon commonly called parallax error.

The physical overlap between the images, the geometric constraints on imaging system position, and the type of mapping between images are considered to be the major parameters influencing the stitching procedure (Ziv et Josckowicz, IEEE Trans. on Med. Im., 23(1):1-9). Information related to imaging system translation is either provided by the motion control system in automated motion, or by image analysis methods. Early prior art stitching methods which were based on image analysis rely on identification of specific features in consecutive pictures. However, detection and alignment of prominent anatomical features in x-ray fluoroscopic imaging is considered unreliable and occasionally inaccurate. Therefore, other methods using artificial markers specifically positioned within the FOV were developed, as for example described in EP 1 632 181. When one or several markers, being localized precisely in the plane, are present in two consecutive images, the exact translation can be computed accordingly.

Alternatively, Ziv and Joskowicz propose a method for focusing the panoramic image about the true ROI using a manual phase in which the user indicates the edges that are to be "in focus" and the POI is set accordingly [Ziv et Josckowicz, IEEE Trans. on Med. Im., 23(1):1-9].

A software and hardware package commercially called "SmartStitch" is distributed by CMT Medical Technology Ltd. of Yogne'ham, Israel. The package allows for acquisition of several digital x-ray images wherein the x-ray source and detector are moved in parallel relative to the patient between shots and the patient is held still. An x-ray ruler operative to generate ruler marks on the X ray images is placed alongside the patient. In order for the stitching to be successful, the ruler must be positioned at the same distance from the source as the anatomic features of interest, for example spine or legs. The stitching operation involves alignment of the ruler marks in the regions of overlap between successive images. The resulted panoramic image provides a focused accurate image for features in the plane of the ruler but not in other planes. SmartStitch does not provide a solution for cases where the POI and anatomic features therein are tilted relative to the imaging system and it's motion. Similar packages are provided by other vendors of DR and CR systems.

Some other solutions to obtain panoramic views by stitching multiple X-ray images can be found in the following patents:

EP 0 655 861 and corresponding U.S. Pat. No. 6,097,833 provides an image composition method by overlapping a series of consecutive sub-images acquired by an x-ray source and image intensifier translated along the length of the patient. In order to match accurately consecutive sub-images in the stitching process, the shift between two positions of the imager is determined by finding maximum correlation between the pixel-values in overlapping portions. The above references also suggest the use of an x-ray ruler embedded in the table on which the patient lies. However, they do not propose a solution of how to reconstruct focused images at any POI.

EP 1 255 403 relates to an image composition method for use in digital x-ray imaging. The apparatus consists of a mobile detector, that can be translated along an axis in front of a static x-ray source having a specific collimator enabling the synchronized orientation of the cone beam with the detector positions. The same effect can be obtained by variably tilting the X ray source as the detector is moved without changing the focal spot position. This method eliminates the stereovision-like geometric distortion but cannot be implemented in standard C-arm equipment since on a C arm the source and the detector move together.

U.S. Pat. No. 5,123,056 to Wilson provides a processing and display technique for panoramic images of a whole leg in peripheral angiography setting, based on processing and display of high resolution images and low resolution images, wherein alignment of overlapping images is achieved by a manual or automatic optimization of the visual appearance of features in the POI.

U.S. Pat. No. 5,833,607 to Chou et. al. and U.S. Pat. No. 6,101,238 to Murthy et. al., both assigned to Siemens AG, Germany described other image composition methods for use in peripheral angiography. The x-ray examination apparatus consists of a motorized C-arm which acquires overlapping images by simultaneous translation of the x-ray source and the image intensifier. The images are processed to emphasize certain features and are aligned by detecting and matching meaningful features on a reconstruction plane.

This survey of the prior art shows that most of the methods used for creating panoramic views based on multiple x-ray images are based on expensive and bulky systems that cannot be used intraoperatively. Moreover, some methods developed specifically for x-ray fluoroscopic panoramic imaging, preferably use the position of the x-ray source of the apparatus as reference for stitching consecutive images. All of these systems at least partially correct the parallax error at a specific plane, but the POI is hard to manipulate. Also, these systems are unable to provide a metrical system that can enable the surgeon to measure features lengths and orientations on the resulting image It is therefore an object of this invention to provide a system that can be used to obtain x-ray panoramic views of a region of interest, larger than the field of view of the imaging apparatus.

It is another object of this invention to provide a system that can provide such x-ray panoramic views of a region of interest, focused at a POI adjustable by the operator according to the anatomy of interest.

It is still another object of this invention to provide a method for stitching multiple x-ray images and compose a panoramic view, based on specific features appearing in consecutive images where the specific features are not necessarily positioned in the POI.

It is still another object of this invention to provide a system that can be adapted to a mobile C-arm fluoroscopic machine in an operating room to obtain panoramic views intraoperatively.

It is still another object of this invention to provide the possibility of performing metric measurements in the reconstruction plane.

It is a further object of this invention to provide the possibility of inserting an additional image in a composed panoramic image.

Other objects and advantages of present invention will appear as the description proceeds.

SUMMARY OF THE INVENTION

The present invention is a method and system for generating a panoramic image based on a set of partially overlapping images, such as those produced by a radiation based imaging device or system. According to some embodiments of the present invention a panoramic image of a region of interest (ROI) which is larger than a field of a view of the radiation based imaging device may be generated by positioning a set of markers along the ROI. The imaging device may acquire a set of images along the ROI, wherein the acquired images may have at least partially overlapping portions. Image processing logic, which may be part of a dedicated image processing system or may be code running on a general purpose processor, may align at least two separate images by aligning a common marker found in both images and may compensate for a difference between the distance from a radiation source to the marker element and the distance from the radiation source to a plane of interest. According to further embodiments of the present invention, a rendering module, which may part of a dedicated image processing system or code running on a general purpose processor, may combine substantially all the aligned images by generating a data set including pixel values of the combined images such that corresponding pixels of overlapping image portions are combined.

According to some aspects the invention, the radiation based imaging device/system may be x-ray based. According to a method of obtaining an x-ray panoramic image of a region of interest (ROI), focused in a selected plane of interest (POI), the following steps may be implemented:

a) positioning stitching markers along the ROI;

b) using an x-ray system comprising an x-ray source and a detector to acquire multiple x-ray images covering an ROI larger than the field of view (FOV) of the x-ray system;

c) detecting the marker elements in the separate x-ray images;

d) aligning the separate x-ray images according to the marker elements;

e) readjusting the separate x-ray images and/or their alignment to account for the difference between the distance from the x-ray source to the surface of the marker elements and the distance from the x-ray source to the POI; and f) constructing the resulting panoramic image by selecting or composing, for each pixel, a value from the appropriate pixels in the appropriate separate x-ray images.

The method is characterized in that the stitching markers are positioned such that they are not necessarily positioned within the selected POI; however, they show in all relevant images. The method of the invention can be applied intraoperatively.

The acquired images can be fluoroscopic images acquired with a mobile fluoroscopic C-arm. In other embodiments the x-ray system can be a radiographic system and the detector a digital radiography detector, or the x-ray system can be a radiographic system and the detector a computer radiography plate, or the x-ray system can be an angiographic fluoroscopy system and the method is applied to imaging of the cardiovascular system.

In embodiments of the method the operator can interactively change the POI multiple times based on a single acquisition of individual x-ray images. In different embodiments the x-ray source and detector are moved relative to the imaged subject automatically, the x-ray source and detector are moved relative to the imaged subject manually, or the x-ray source and detector are still and the imaged subject is moved relative to them.

In preferred embodiments of the method of the invention the acquired images overlap to the extent that only the center of each image is used to form the panoramic image.

Aligning the separate x-ray images to form a single image may comprise aligning the markers such that the same markers in adjacent images overlap and may include one or both of the following types of motion of the image planes: translations and rotations around the imaging axis.

Readjusting the alignment of the separate x-ray images to account for the difference between the distance from the x-ray source to the POI and the distance from the x-ray source to the surface of the marker elements may comprise re-scaling the images around their imaging center by the ratio between the two distances or may comprise translating the separate images relative to each other without scaling.

In an embodiment of the method the step of composing a panoramic image focused at the POI comprises the following steps:
 i) creating a 3D geometric model of separate x-ray images aligned on the marker elements surface, the x-ray images sources and their orientations;
 ii) calculating the 3D location of the POI in the 3D model;
 iii) defining a continuous objective function matching each panoramic image pixel (or point) with a 3D POI point;
 iv) locating in the separate x-ray images, for each pixel in the target image and its corresponding 3D POI point, the pixels, or sub-pixel points, that correspond to x-rays passing through the POI point.

In embodiments of the method of the invention, selecting or composing, for each pixel in the resulting panoramic image, the value of the appropriate pixel in the appropriate separate x-ray image comprises any one of the following:
 i) choosing the pixel which is closest to the center in its original x-ray image;
 choosing an average value of the original pixels;
 iii) choosing a weighted average; or
 iv) choosing the maximal or minimal gray level value.

In embodiments of the method the POI can be selected by using any one of the following:
 a) anatomical or artificial markers that determine a specific point in the POI;
 b) a ruler which indicates the height and orientation of the POI;
 c) manual indication of the height and the orientation of the POI;
 d) tuning buttons to gradually change the height and the orientation parameters of the POI on a display device.

The acquisition of the images can be performed by a fluoroscopic system in a continuous pulse mode, by a fluoroscopic system in a standard continuous mode, optionally, with image de-blurring processing, or by a fluoroscopic system in a standard pulse mode, optionally, with additional information relating to ROI coverage and image quality that is displayed for the operator.

The panoramic image acquired using the method of the invention allows for various types of angle and distance measurements along the POI. The panoramic image may show a ruler device, which was laid in the ROI, wherein the ruler device allows measurements of spatial angles and distances, wherein the measurements are not restricted to the POI.

The method of the invention can be used for planning a correct trajectory over a ROI larger than the FOV. It can also be used for visualizing and positioning virtual templates of medical implants and tools within the panoramic image scene.

In embodiments of the invention an additional image showing a drill guide, a ruler, or another type of surgical tool is inserted into the panoramic image after the panoramic image is obtained.

In embodiments of the invention, after the panoramic image is obtained, a new image of a portion of the panoramic image is captured showing a change in orientation or structure of an anatomical or other feature and a new panoramic image is computed incorporating the new image and adjusting the whole panoramic image for the change in orientation or structure.

In another aspect the invention is a system for obtaining an x-ray panoramic image of a region of interest (ROI), in a selected plane of interest (POI). The system comprises:
 i) an x-ray apparatus capable of acquiring multiple x-ray images comprising an x-ray source and a detector;
 ii) a set of stitching markers that are placed in the FOV; and
 iii) a computer and dedicated software that are adapted to processes the acquired multiple x-ray images and compose a panoramic image from the acquired multiple x-ray images.

The system is characterized in that the stitching markers are configured such that they do not necessarily have to be positioned within the selected POI, however they are positioned such that they show in all relevant images; and, the apparatus is adapted such that it can be moved relative to the imaged subject from image to image such that there is an overlap between the images.

Embodiments of the system of the invention can also comprise a display system.

The stitching markers can be included in a rigid structure, in a radiation translucent flexible structure, or they may comprise a continuous marker.

Embodiments of the system are adapted to allow detection of the stitching markers in the separate x-ray images automatically, using computer vision algorithms. In other embodiments the system is adapted to allow detection of the stitching markers in the separate x-ray images manually by allowing the user to indicate to the system where the stitching markers are visible on the separate x-ray images, using a pointing device.

In embodiments of the system the x-ray apparatus is a mobile fluoroscopic C-arm, a radiographic system and the detector is a digital radiography detector, a radiographic system and the detector is a computer radiography plate, or an angiographic fluoroscopy system adapted to allow imaging of the cardiovascular system.

In embodiments of the system it is adapted to allow the operator to interactively change the POI multiple times based on a single acquisition of individual x-ray images.

The x-ray source and detector can be moved relative to the imaged subject automatically or manually or the x-ray source and detector can be stationary and the imaged subject is moved relative to them.

BRIEF DESCRIPTION OF THE DRAWINGS

The subject matter regarded as the invention is particularly pointed out and distinctly claimed in the concluding portion of the specification. The invention, however, both as to organization and method of operation, together with objects, features, and advantages thereof, may best be understood by reference to the following detailed description when read with the accompanying drawings in which:

DETAILED DESCRIPTION OF THE INVENTION

The invention relates to the specific acquisition of multiple overlapping x-ray images, the dedicated algorithms which compute the stitching parameters, the system which controls the panoramic image formation and visualization and the associated medical or other applications that make extensive use of such a panoramic image. The invention relates both to a system that presents novel methods of construction of panoramic images and to novel applications that are based on the panoramic images. The system can be part of an x-ray imaging machine or an independent system which receives the image from an x-ray imaging machine, either by sampling the video output or by using digital connectivity. The x-ray imaging machine may be a fluoroscopic machine or a machine that takes one image at a time and is capable of taking a series of images. As used herein the plane of interest (POI) is not necessarily limited to a single spatial plane. The POI can be any continuous spatial surface located between the x-ray source and the detector.

Figure 1:
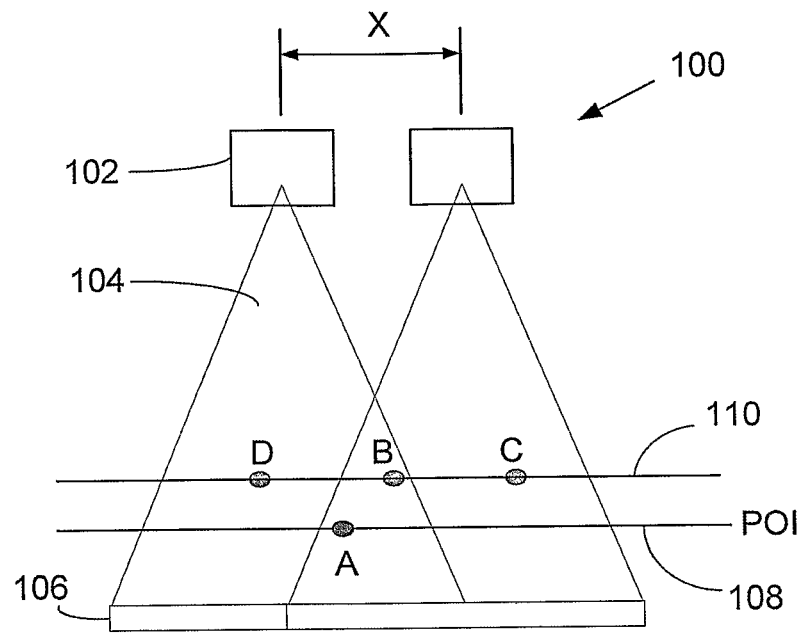
FIG. 1 schematically illustrates the geometrical difficulties in generating a panoramic image.
Figure 2:
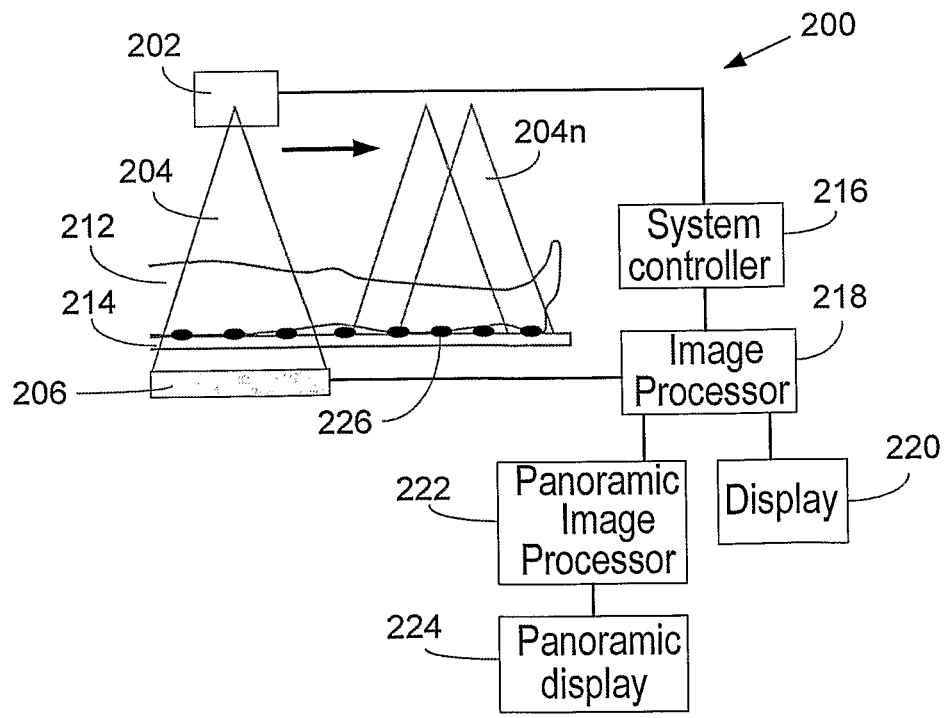
FIG. 2 schematically illustrates the system of the invention.

Referring now to FIG. 2, system 200 is an embodiment of the present invention. X-ray source 202 emits cone beam 204 which is received by detector 206. Detector 206 may be an image intensifier, flat panel detector or any other x-ray area detector known in the art. Patient 212 is positioned on patient support 214 in the space between the source and the detector. In different embodiments the patient may be lying, sitting or standing and the source-detector set up may be in different orientation relative to the example of FIG. 2. The X-ray source 202 and detector 206 are mounted on a gantry (not shown in the figure), such as a fluoroscopic C-arm or other gantry known in the art and are made to move together relative to the patient and generate a series of x-ray exposures as indicated in FIG. 2 by a first beam 204 and last beam 204n. For clarity the plurality of beams emitted during translation are not shown. It is to be noted that in other embodiments of the system the patient support 214 with the patient on it can be moved relative to a stationary imaging system. The operation of the x-ray source and data acquisition are monitored by system controller 216. Attenuation data for x-rays that have been attenuated by patient 212 and detected by detector 206 are acquired and processed by image processor 218 and optionally displayed on display monitor 220. In addition, according to the invention the images are processed further by panoramic image processor 222 and may be displayed by panoramic display monitor 224. System controller 216, image processor 218 and panoramic image processor 222 may be integrated onto one hardware system or operate on separate hardware systems. Likewise, the display monitors 220 and 224 may be integrated or separated according to the specific application.

The process of aligning the captured x-ray images with respect to one another uses radiation absorbing marker elements that can be automatically detected within each image. These markers are marked 226 in FIG. 2 where they are shown by a way of example to be mounted on patient support 214. The functionality of these marker elements 226 is further described hereinbelow.

The system of the present invention comprises:
an X ray machine capturing multiple images covering an ROI larger than the FOV;
a set of marker elements placed within the FOV;
a computer, which runs computer software for creating a single image of the whole ROI The method of the invention for the construction of the panoramic image is based on assuring that a sufficient overlap between the images is achieved in the acquisition process. Considering, for example, an embodiment using mobile fluoroscopic C arm, the system uses preferably the "continuous pulse" mode. This means a series of images are taken at short intervals with large overlap between consecutive images. Unlike the pulsed mode, this mode of operation provides multiple images each second (for example, up to 12 pictures per second using a GE OEC 9800 C-arm). The advantage of the continuous pulse mode is that it provides sharp images unlike the multiple blurry images acquired in continuous mode. If the c-arm does not support a "continuous pulse" mode, one can use the standard continuous mode, preferably with post image de-blurring processing. Alternatively, one can use the standard pulse mode. in this case, the capturing process is preferably coupled with a display of additional information. The additional information comes to ensure the necessary overlapping between images of sufficient quality. In a preferred standard pulse embodiment, the system provides the operator with feedback related to ROI coverage and image quality, e.g. dynamic range, noise, video formation, etc. The feedback can be graphical. If the stitching markers have a predefined configuration, the system automatically detects which areas of the ROI have not been captured well yet, and displays that information.

The C-arm can be moved by either mechanical or manual means. In a preferred embodiment of the invention, for example, the operator pushes a C-arm gantry that has wheels along the ROI, for example, a patient's leg. The C-arm motion does not have to maintain a constant velocity. The only requirement on its speed is that it must be slow enough to enable enough overlap between consecutive images, wherein the required overlap depends on the required accuracy and the spacing of the markers. The C-arm motion does not have to follow a straight line, nor it is constrained to a single plane, but the image planes are required to be parallel in all images.

Preferred embodiments for creating a panoramic view of an ROI according to the invention use the following information:

a) Separate x-ray images obtained with a sufficient overlap, containing a set of marker elements, visible in the x-ray images. The image planes of all x-ray images are required to be parallel but rotation of the imaging device around axis from the x-ray source to the detector is allowed.

b) The distance from the x-ray source to the marker's surface (the surface on which the marker elements are positioned) at each separate x-ray image. This information can either be fed into the system manually, or, preferably, deduced automatically by the system, using, for example, the size of the marker elements. A skilled engineer proficient with image processing should have no trouble designing marker elements and creating computer software that re-construct the distance of the surface of the marker elements from the x-ray source, for each separate x-ray image, given the geometrical model of the x-ray machine.

c) Distance of the POI from the x-ray source for each separate x-ray image. This again can be done manually or automatically, as is described herein below.

d) Embodiments in which the x-ray source motion is not restricted to a single plane additionally use information describing either the motion of the imaging device or the shape of the marker elements surface.

Preferred embodiments of the method of the invention for creating a panoramic view of an ROI comprise the following steps:

a) Positioning stitching markers along the ROI: By markers is meant X-radiation opaque objects of a defined shape which are seen in the X-ray images, such as elements 226 in FIG. 2. Dedicated stitching markers are positioned such that they show in all relevant images. However, they are not necessarily positioned within the POI. This relaxation of the constraints on the possible locations of the markers enables to position the markers away from the operated area and so simplify the operation room procedure. Stitching markers may be included in a rigid structure, e.g. metal balls embedded in rigid radiation translucent material, which may facilitate the detection of the markers in the image and the reconstruction of the marker position. Alternatively, the stitching markers can have a radiation translucent flexible structure, e.g. metal balls embedded into a plastic strip which does not limit their positioning in space. Alternatively a continuous marker can be provided such as known in the industry as x-ray ruler.

b) capturing multiple images covering an ROI larger than the FOV;

c) detecting the marker elements: The system first detects the marker elements in the separate x-ray images. This can be done either automatically, using computer vision algorithms that may vary according to the shape of the markers, or manually. In the manual case the user indicates to the system where the marker elements are visible on the separate x-ray images, using a pointing device, e.g. a computer mouse.

d) spatially aligning the separate x-ray images according to the marker elements: The images are aligned such that the same markers in adjacent images overlap. Alignment may include both translations and rotations in the plane. The resulting alignment is focused at the surface of the marker elements, which is not necessarily the POI. Note that in some cases, where the marker elements are not all in the same plane parallel to the imaging plane, the marker elements suffer from parallax error as well. This means that accurate alignment can not be achieved over all the marker elements. In this case, the alignment should emit some of the markers. The marker elements surface will only include marker elements that were used in the alignment process. Also, if the x-ray source was closer to a specific marker element in one x-ray image than in the other, the separate x-ray images have to be re-scaled accordingly.

e) Height adjustments: The system then readjusts the alignment of the separate x-ray images in the panoramic image to account for the difference between the distance from the x-ray source to the POI and the distance from the x-ray source to the surface of the marker elements. One way of doing this is by re-scaling the images around their imaging center by the ratio between the distance from the POI to the x-ray source and the distance between the marker elements surface and the x-ray source at the image center. This ratio is known as the image magnification ratio. Scaling the images around their center achieves two goals: firstly, the alignment of the images is correct for the POI at the separate x-ray images centers; and, secondly, the scaling of the images brings them all to the same scale in terms of the number of pixels per millimeter. In cases in which there is only small overlap between images, it is possible to adjust the images for the height differences by using transformations other than scaling. These other transformations may be nonlinear.

Another way of adjusting the alignment of the separate x-ray images in the panoramic image to account for the difference between the distance from the x-ray source to the POI and the distance from the x-ray source to the surface of the marker elements, is by moving the separate images without scaling. This means that the realignment of the images is obtained by applying to each separate image a different translation motion, i.e., images are pushed closer together or further apart, according to their relative image magnification ratios. The result is an image in which similar objects closer to the x-ray source appear larger than those farther away from the x-ray source. The resulting image will be more similar to an actual x-ray image taken from a single source, however, measurements on it will be non-linear.

f) Panoramic image construction: After alignment of the separate x-ray images, and adjusting them for their magnification ratio, the system constructs the resulting panoramic image by selecting or composing, for each pixel in the resulting image, a value from the appropriate pixels in the appropriate x-ray images. If such appropriate pixel occurs in more than one x-ray image, the preferred embodiment of the invention uses the pixel which is closest to the center in its original x-ray image in order to minimize image distortion. For this pixel, the x-rays are closest to perpendicular to the imaging surface. Other embodiments may use an average value of the original pixels, a weighted average, the maximal or minimal gray level value, or any other decision rule.

Some embodiments of the method of the invention for creating a panoramic view of an ROI use another way of composing the panoramic image such that it is focused at the POI. In these embodiments the original images or their respective alignment are not adjusted as described above. Instead, step e above is replaced by the following steps:

i) A 3D geometric model of the marker elements surface, the x-ray images sources and their orientations is created. The 3D model is created using the alignment of the images according to the marker elements, the distances between the x-ray source and the marker elements surface at each image, and (possibly) information about the height of the x-ray source or the shape of the marker elements surface.

ii) The 3D location of the POI is calculated in the 3D model.

iii) A continuous objective function matching each panoramic image pixel (or point) with a 3D POI point is defined. Examples of such functions include a function that corresponds to an orthographic projection and a function preserving geodesic distances (in case the POI is embeddable in a plane).

iv) For each pixel in the target image and its corresponding 3D POI point, the pixels, or sub-pixel points, that correspond to x-rays passing through the POI point are located in the separate x-ray images (at most one per image).

Finally for each pixel in the target image its value is selected or composed from the values of the matching pixels from the separate images using one of the decision rules described in step f above.

Figure 8A:
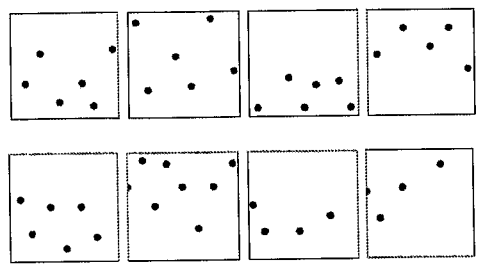
FIG. 8A to FIG. 8D illustrate the steps of the method of the invention for creating a panoramic view of an ROI.
Figure 8B:
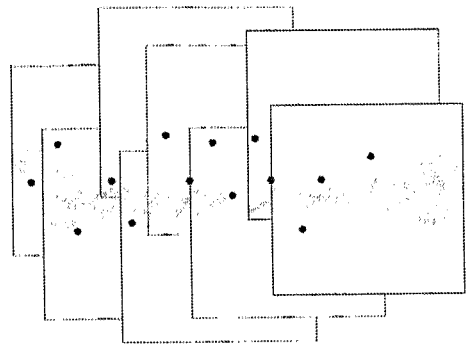
Figure 8C:
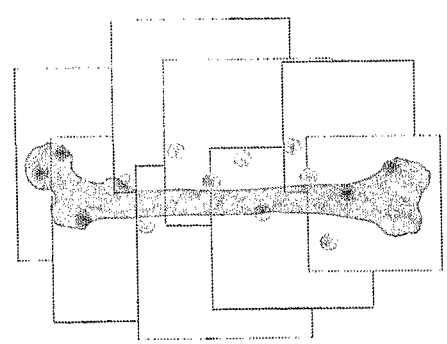
Figure 8D:
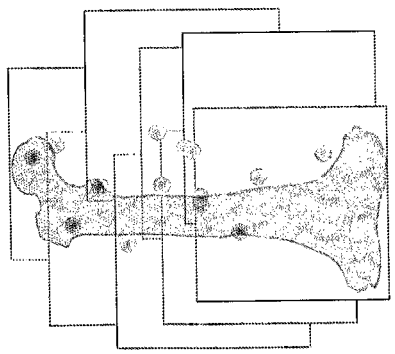

FIG. 8A to FIG. 8D show a schematic example illustrating various steps of the procedures described above. In FIG. 8A is shown a group of captured images with the marker elements visible. In FIG. 8B is shown a panoramic image stitched using the markers. The bone is shown out of focus. In FIG. 8C is shown a panoramic image composed of scaled images with a bone in focus and the markers out of focus (the bone is close to the marker on the left side and gets closer to the X-ray source towards the right). In FIG. 8D is shown a panoramic image that is focused at the bone by translating the original images in the plane according to bone height. Again, the marker elements are out of focus.

Acquisition with high overlap between images spares the user from determining the height difference between the POI and the marker elements identifiable in the image or at least minimizes the errors associated with not using or with using approximated measurement of this height. The error in taking only the center area of each image is reduced because the imaging rays are nearly perpendicular to the POI, and the need of height dependant resealing interpretation of the image is reduced While acquisition of multiple images with high overlap is desirable, in other embodiments of the invention only a few overlapping images are acquired, for example two or three images in digital radiography of the spine or the lower extremities.

Figure 3:
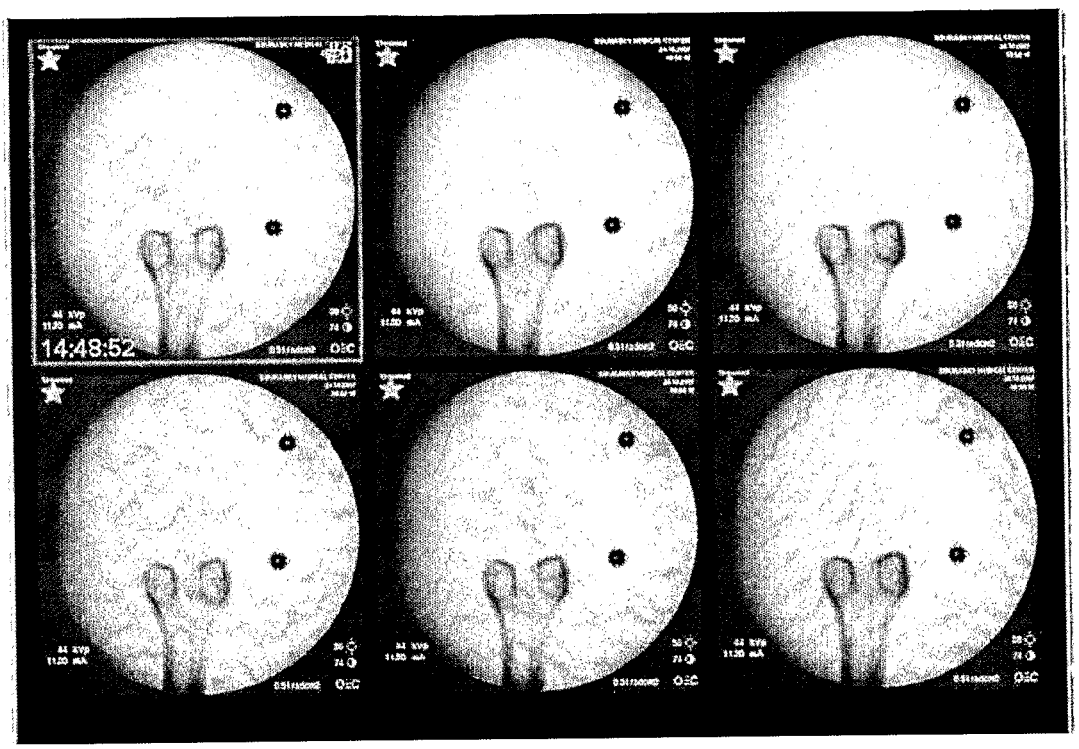
FIG. 3 shows separate x-ray fluoroscopic images with the stitching markers detected and marked on them.
Figure 4:
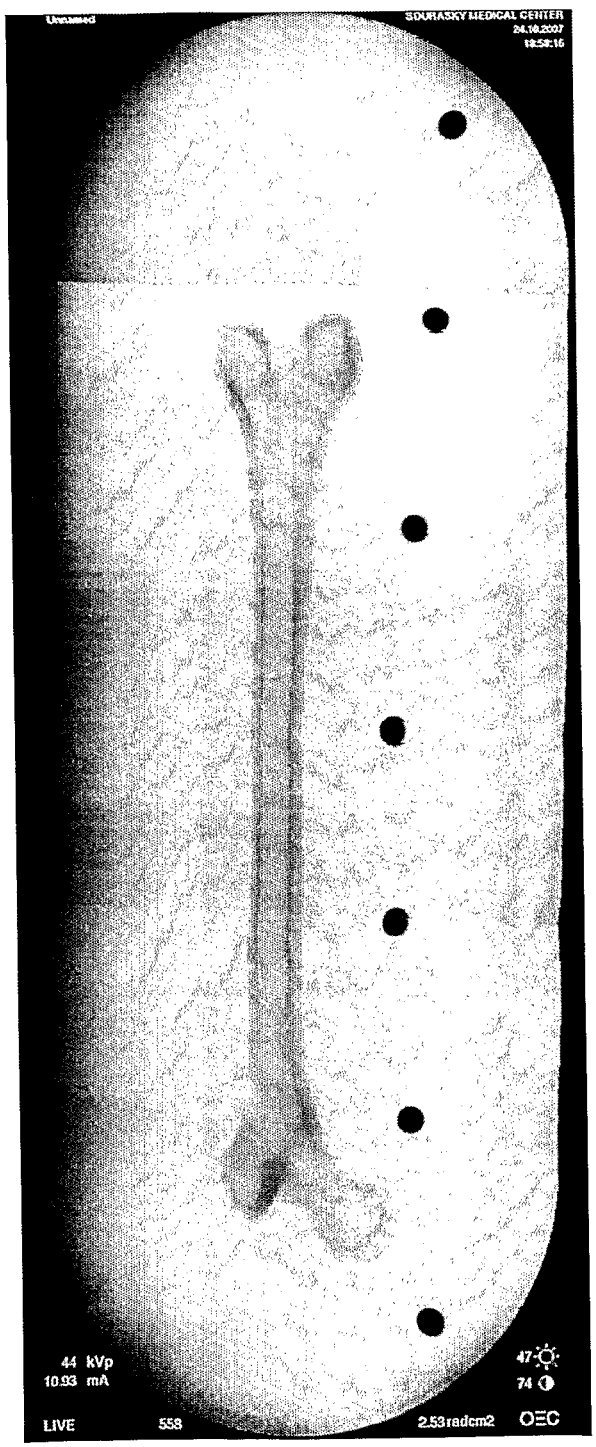
FIG. 4 shows the panoramic image resulting from the stitching process.

FIG. 3 shows a series of six fluoroscopic x-ray images of a femoral distal end. The images are consecutive images taken as a part of a longer series using an OEC 9800 Vascular c-arm machine, in a 12 pulse per second (PPS) CINE mode, which constitutes the continuous pulse mode mentioned earlier. The typical circular shape of the C-arm FOV can be noted. The star next to the images means that algorithm applied by the software program of the system found these images suitable for being used in the stitching process. The stitching markers laying on the patient support table and appearing as black dots on the images, are identified by the software of the system and tagged with a circle. In this particular series of shots, 154 images were taken while the C-arm was moved relative to the patient and used to compose the panoramic image shown in FIG. 4.

After stitching the consecutive fluoroscopic x-ray images together and composing the panoramic view focused at the plane of the markers, the present invention enables the user to select a specific POI corresponding to anatomic feature of interest and compose for it a focused panoramic image. The POI depth information can be obtained in several ways including:

a) Using corresponding image points: Consider, for example, a sharp edge of a bone of interest or a small marker attached to such bone. Since the X-ray source motion is already known, this real world point within the POI may be detected in consecutive images, and its three dimensional coordinates with respect to the moving X-ray source may be calculated by triangulation revealing POI depth. A small number of POI points is usually sufficient for defining the distance to the POI everywhere.

b) Using one or more rulers which indicates the height and orientation of the POI, as described in the pending Israeli Patent application IL 184151 by the applicant of the present application, the description of which, including publications referenced therein, is incorporated herein by reference. By aligning the ruler with the POI, for example, by mounting the ruler in a known position and orientation with respect to the bone, the POI position and orientation are revealed.

c) Feeding in manually the height of the POI at several locations along the panoramic view. One option is feeding the POI depth with respect to the plane of the markers.

d) Using tuning buttons (defined hereinbelow).

Tuning buttons are particularly useful in obtaining quality panoramic images focused in the desired POI, thereby avoiding critical anatomical features from looking blurred, doubled or "out of focus". Tuning buttons are preferably GUI buttons, available in the software program displaying the panoramic image, but can also be physical buttons used to give feedback to the computer software. The user can employ tuning buttons to gradually change the selected POI, while the system corrects the panoramic image in real time, until the desired features appear "in focus". This tuning procedure can be done at one specific location on the panoramic image creating a POI of constant height, or at several locations on the panoramic image, thus creating a segmented POI with different heights according to the position in the image. In another embodiment, the software detects observable objects like anatomical features or surgical tools in neighboring images. From their relative position, the software can calculate if they are above or below the specified POI, and tag them with colors describing their height. As the user tunes the height of the POI, the color of the selected features is changed accordingly, until the user is satisfied with the image.

Figure 5:
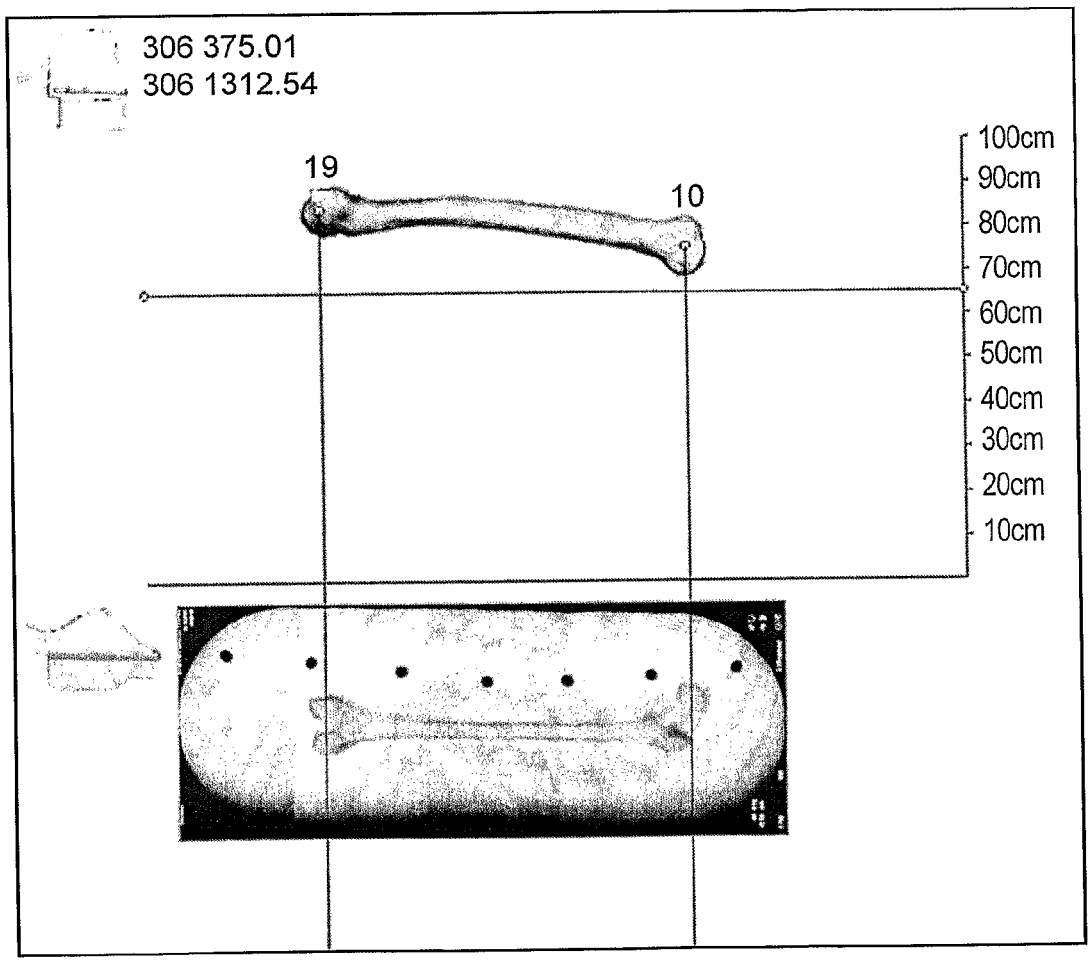
FIG. 5 shows the interface used for determining the POI after the images have been aligned at the height of the markers.

FIG. 5 shows a screenshot of a Graphical User Interface (GUI) of an embodiment of a system of the invention. The left side of the screen shows the height of the C-arm ends, the lower part representing the source of the x-rays, located at height 0 cm and the top part representing the image intensifier used as x-ray detector. The line situated at about 65 cm represents the (known at this stage of the process) height of the stitching markers with respect to the x-ray source, i.e. the height of the patient table on which they lie. A panoramic image composed of images stitched to be focused in the plane of the marker elements can be seen in the bottom part of the screen. In this particular case, the markers are very close to the bone that is the ROI, and so the bone does not appear to be "out of focus", as is generally the case if the markers are not close to the POI. A virtual feature of the anatomy, a femoral bone in this example, is graphically displayed in the upper part of the screen. The software program asks the user to give the exact spatial position of the bone within the space delimited by the ends of the C-arm scan. To do that, the user should point out the horizontal position of the femur head and the knee on the panoramic image below and to specify their height (using the plane in which the markers lie as reference). In more complicated situations more points are needed in order to reconstitute the entire bone, for example, three points for a whole leg (femur and tibia) scan. In the manual mode, the user measures the actual heights of both ends of the bone and enters them in the software of the system (or drags the ends of the virtual bone with a mouse), and they are displayed on the screen. In the example shown in FIG. 5, the knee is elevated 19 cm above the markers (the table) and the femur head is elevated 10 cm above the table. In the automatic mode, one or more positioning markers can be placed for example on the patient's knee to determine its height, thereby making part of the procedure automatic since the markers can be designed in such way that the vertical scale on the image indicates their height accurately.

As said herein above, in preferred embodiments of the invention only the center part (with respect to the length direction) of each acquired image is used in the composition of the panoramic image. Considering now an imaging system which has a round, square or wide rectangular field of view, the "leading" section and "trailing" section of each image (except for the end images) is not used in the panoramic image. According to some embodiments of the invention a collimator is provided to collimate the beam to a (wide) fan shape so that, while overlap is kept between successive images, less area of each image is not being used. The collimator may be provided as a part of the C-arm system, in which case it is adjusted to a rectangular shape. In imaging systems that are not equipped with an appropriate adjustable collimator, an external collimating plate with appropriate beam opening can be provided and installed anterior to the patient. Care should be taken to assure there are still stitching marks in the overlap of any pair of successive images. The advantage of using a collimator in this fashion is in the reduced x-ray dose to the patient.

Figure 6:
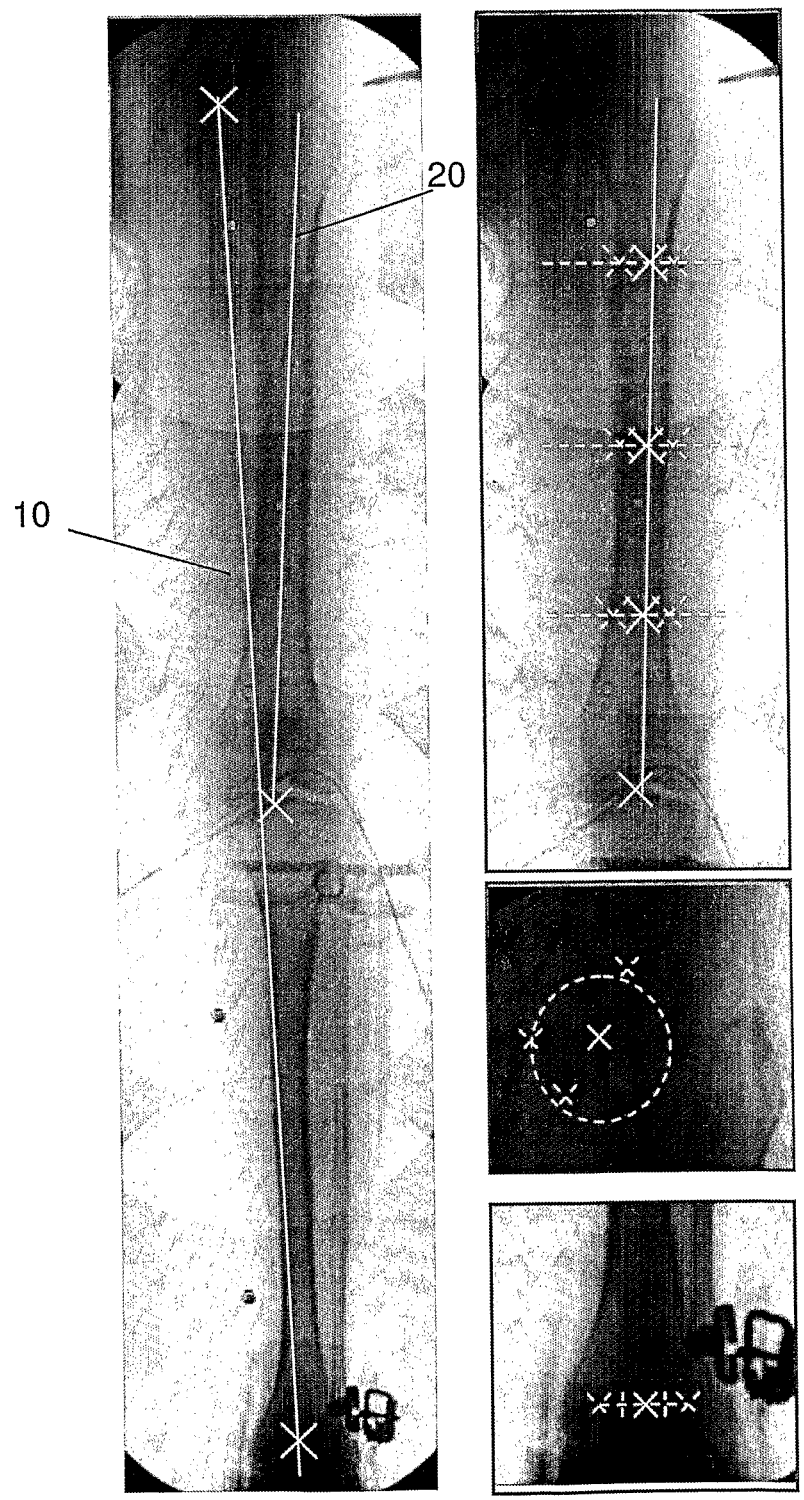
FIG. 6 shows an estimation of the anatomical and mechanical axes in the lower limb.
Figure 7:
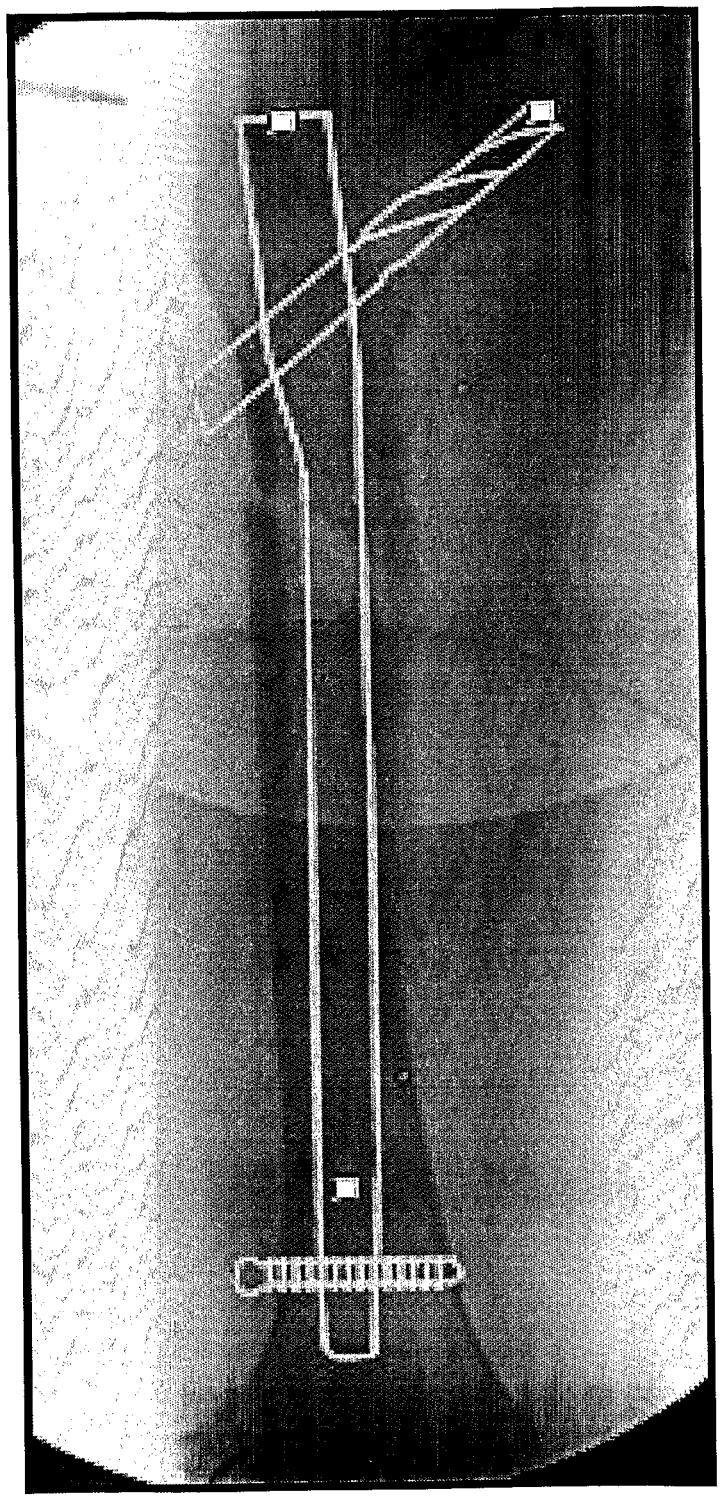
FIG. 7 is a panoramic image of a long proximal femur nail template positioned on a femoral bone.

The method and system of the invention for image stitching is applicable to any part of the body, allowing the implementation of novel panoramic view based applications, for example:

a) A panoramic image which includes multiple joints can be used for estimation of the anatomical and mechanical axes of interest. It further allows for various types of angle and distance measurements. Measurement procedures are indicated for deformities such as scoliosis and for trauma operations. FIG. 6 shows for example an estimation of the anatomical and mechanical axes in the lower limb Anatomic Femoral Axis is in 6 degrees of valgus from the mechanical axis of lower limb. On the left side, a panoramic image, with both axes drawn, is shown. On the right side, the top picture shows the definition of anatomical femoral axis, the middle picture shows femur head center, and the bottom picture, the center of distal tibia.

b) After a panoramic image is created the system can enable the user to make measurements of angles and distances on the image by creating a two dimensional calibration using a marking device ruler as described in the previously described Israeli patent application IL 184151. The measuring device is laid in the ROI and appears in the images that are stitched together to form the panoramic image. Using this calibration, a measurement in pixels can be translated to millimeters not only along the POI but also along any three dimensional direction defined by the ruler device.

c) The method of the present invention can be used to plan the correct trajectory over a region of interest (ROI) larger than the FOV defined by the fluoroscopic machine. Moreover, with the method of the invention, it is possible to plan and visualize templates, i.e. graphic overlays representing a tool or device, that are larger than the normal FOV. A dynamic assessment of the template position is achievable based on the analysis of the current position of a guide wire with incorporated markers as described for example in the previously referenced Israeli patent application IL 184151. This assessment allows the surgeon to examine a correct position for the template as a whole. FIG. 7, for example, displays a template of a long proximal femur nail (PFN) on a panoramic image of the femur. This figure is made possible by using the "templating" feature of IL 184151 over the panoramic image of the present invention. The method of the present invention can be used to follow the operation procedure in the operating room with the possibility of inserting an additional image in a composed panoramic image. For example, after having created a panoramic image of the full leg (see e.g. FIG. 6), the surgeon may hold a drill guide or a ruler as described in Israeli Patent application IL 184151 on the femur head and take another fluoroscopic image. The orientation of the additional image is determined from the markers shown in it, and its correct stitching into the panoramic image is computed. The alignment of the additional image within the panoramic image enables the guide to also be seen in the panoramic image. Furthermore, it enables other features, for example, to visualization of the trajectory of a drill or display an implant template for the surgeon.

In another example of inserting an additional image in a composed panoramic image, the surgeon can first create a panoramic image of the entire leg. He then changes the angle of the knee or the bone, e.g. High Tibial Osteotomy (HTO) procedure, and then takes another image of the knee (or bent bone area) only. The system identifies that the additional image is only of the knee and updates the panoramic image accordingly to account for the local angle change.

d) The method can be used in non-destructive testing or homeland security applications wherein, for example, an item larger than the FOV of the imaging system can be scanned by a series of cone beam x-ray images in the presence of stitching markers. The method can then be used to reconstruct a series of panoramic images, each focused at a different height within the item.

Embodiments of the invention have been described by way of non restrictive examples with reference to image acquisition by fluoroscopic C-arm in an operating room environment. However, the invention can be applied to other X ray imaging systems and other clinical or non-clinical settings. For example the invention is applicable to cardiovascular angiographic imaging systems wherein panoramic views of long blood vessels are required. It is also applicable to digital radiography and computed radiography wherein panoramic images of anatomy longer than the length of the imager are sometimes required, for example an image of the full spine or the legs. Further, the invention is applicable to non-human x-ray imaging, e.g. in non-destructive testing and homeland security.

Although embodiments of the invention have been described by way of illustration, it will be understood that the invention may be carried out with many variations, modifications, and adaptations, without exceeding the scope of the claims.

The invention claimed is:

1. A system for obtaining a panoramic image of a region of interest (ROI), focused in a selected plane of interest (POI), said system comprising:
   stitching markers visible in an x-ray image;
   an x-ray system comprising an x-ray source and a detector adapted to acquire a set of multiple x-ray images covering an ROI larger than a field of view (FOV) of said x-ray system, wherein the set of multiple x-ray images is acquired while the x-ray source is positioned in a substantially parallel orientation along a set of points which points are in a substantially straight line, which straight line is substantially perpendicular to the parallel orientation;
   receiving circuitry configured to receive the multiple x-ray images from the x-ray system;
   image processing circuitry configured to construct the panoramic image by:

(1) detecting said markers in the multiple x-ray images;
(2) aligning the multiple x-ray images according to said stitching markers;
(3) adjusting the height, from the surface of the markers to said POI, of the focus of the aligned images, by readjusting the multiple x-ray images and their alignment to account for the difference between the distance from said x-ray source to the surface of said markers and the distance from said x-ray source to said POI, wherein said POI is a plane other than the plane of said stitching markers and calculating the height adjustments to be made, to adjust the height of the focus of the aligned images, is based on the appearance of said stitching markers in said multiple x-ray images; and
(4) selecting, for each pixel in the panoramic image, a value of a corresponding pixel in one of the multiple x-ray images.

2. A system according to claim 1, wherein said x-ray system is a fluoroscopic C-arm.

3. A system according to claim 1, wherein, aligning the multiple x-ray images comprises aligning said markers such that the same markers in adjacent images overlap.

4. A system according to claim 1, wherein aligning the multiple x-ray images includes one of the following types of motion of the image planes: translations and rotations around the imaging axis.

5. A system according to claim 1, wherein readjusting the alignment of the multiple x-ray images to account for the difference between the distance from the x-ray source to the POI and the distance from the x-ray source to the surface of said markers comprises re-scaling the images around their imaging center according to the ratio between said two distances.

6. A system according to claim 1, wherein readjusting the alignment of the multiple x-ray images to account for the difference between the distance from the x-ray source to the POI and the distance from the x-ray source to the surface of said markers comprises translating the images relative to each other without scaling.

7. A system according to claim 1, further comprising a collimator coupled to said radiation source and configured to collimate radiation emitted from said radiation source.

8. A system for obtaining an x-ray panoramic image of a region of interest (ROI), in a selected plane of interest (POI), said system comprising:
  i) an x-ray system comprising an x-ray source and a detector, said x-ray system being capable of acquiring a set of multiple x-ray images of the ROI, wherein the set of multiple x-ray images is acquired while the x-ray source is positioned in a substantially parallel orientation along a set of points which points are in a substantially straight line;
  ii) a set of stitching markers visible in x-ray images;
  iii) receiving circuitry configured to receive the multiple x-ray images from the x-ray system; and
  (iv) a computer including dedicated software adapted to process the set of multiple x-ray images and compose, while preserving geodesic distances, a panoramic image of the selected POI from the set of multiple x-ray images, wherein: (1) composing a panoramic image includes adjusting the height, from the surface of the markers to said POI, of the focus of the panoramic image, by readjusting the multiple x-ray images and their alignment to account for the difference between the distance from said x-ray source to the surface of said markers and the distance from said x-ray source to said POI, (2) the selected POI is a plane other than the plane of said stitching markers and (3) calculating the height adjustments to be made, to adjust the height of the focus of the panoramic image, is based on the appearance of said stitching markers in said multiple x-ray images.

9. A system according to claim 8, wherein said x-ray system is adapted to automatically acquire the multiple x-ray images by automatically moving said radiation source and said detector.

10. A system according to claim 8, wherein composing a panoramic image of the selected POI from the multiple x-ray images comprises aligning the multiple x-ray images according to said stitching markers and readjusting the multiple x-ray images and their alignment to account for the difference between the distance from said x-ray source to the surface of said markers and the distance from said x-ray source to said POI.

11. A system according to claim 10, wherein aligning the multiple x-ray images includes one of the following types of motion of the image planes: translations and rotations around the imaging axis.

12. A system according to claim 8, wherein the x-ray system is a mobile fluoroscopic C-arm.

13. A system according to claim 10, wherein readjusting the alignment of the multiple x-ray images to account for the difference between the distance from the x-ray source to the POI and the distance from the x-ray source to the surface of said markers comprises re-scaling the images around their imaging center according to the ratio between said two distances.

14. A system according to claim 10, wherein readjusting the alignment of the multiple x-ray images to account for the difference between the distance from the x-ray source to the POI and the distance from the x-ray source to the surface of said markers comprises translating the images relative to each other without scaling.

* * * * *